United States Patent [19]
Dekker et al.

[11] Patent Number: 5,942,619
[45] Date of Patent: Aug. 24, 1999

[54] **QUINOLONE COMPOUNDS FOR THE TREATMENT OF DISORDERS CAUSED BY *HELICOBACTER PYLORI***

[75] Inventors: Koenraad A. Dekker, Frechen, Germany; Liang H. Huang, East Lyme, Conn.; Taisuke Inagaki, Taketoyo-cho, Japan; Nakao Kojima, Taketoyo-cho, Japan; Yasuhiro Kojima, Taketoyo-cho, Japan; Yuji Yamauchi, Taketoyo-cho, Japan

[73] Assignee: Pfizer Inc., New York, N.Y.

[21] Appl. No.: 09/043,374

[22] PCT Filed: Jul. 11, 1996

[86] PCT No.: PCT/IB96/00670

§ 371 Date: Apr. 24, 1998

§ 102(e) Date: Apr. 24, 1998

[87] PCT Pub. No.: WO97/12868

PCT Pub. Date: Apr. 10, 1997

[30] Foreign Application Priority Data

Sep. 29, 1995 [WO] WIPO .............. PCT/IB95/00812

[51] Int. Cl.⁶ .............. C07D 215/233; A61K 31/47
[52] U.S. Cl. .............. 546/153; 514/312
[58] Field of Search .............. 546/153; 514/312

[56] References Cited

PUBLICATIONS

Chemical Abstracts 109:92736, coppola, 1988.
Chemical Abstracts 108:142529, Huang, 1987.
Marpat 118:22154, Clemence, 1992.
Marpat 118:22153, Clemence, 1992.

*Primary Examiner*—D. Margaret M. Mach

*Attorney, Agent, or Firm*—Peter C. Richardson; Paul H. Ginsburg; Bryan C. Zielinski

[57] ABSTRACT

This invention provides processes for producing quinolone compounds which comprise cultivating Amycoa sp. FERM BP-4785, and then isolating quinolone compounds from the fermentation broth. The compounds produced by these processes include compounds of formula (I) wherein $R^1$ is H, $R^2$ is (a) and $R^3$ is $CH_3$; $R^1$ is $CH_3$, $R^2$ is (a) and $R^3$ is $CH_3$; or $R^1$ is $CH_3$, $R^2$ is (b) and $R^3$ is $CH_3$; and the like. The present invention also relates to a pharmaceutical composition comprising the same, which is useful in the treatment of diseases, disorders and adverse conditions caused by *Helicobacter pylori* and is particularly useful in the treatment of gastroduodenal disorders, diseases and adverse conditions caused thereby.

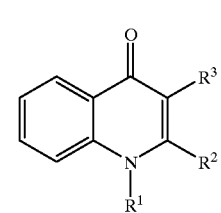

(I)

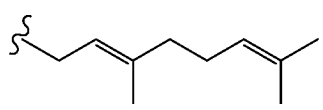

(a)

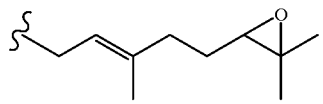

(b)

6 Claims, No Drawings

QUINOLONE COMPOUNDS FOR THE TREATMENT OF DISORDERS CAUSED BY HELICOBACTER PYLORI

This application is a 371 of PCT/IB96/00670, filed Jul. 11, 1996.

TECHNICAL FIELD

This invention relates to novel quinolone compounds, and particularly to novel quinolone compounds produced by fermentation of a microorganism designated as Amycolata sp., which has been deposited as FERM BP-4785. This invention also relates to processes for producing the quinolone compounds, and a pharmaceutical composition comprising the same, which is useful in the treatment of diseases, disorders and adverse conditions caused by *Helicobacter pylori* and is particularly useful in the treatment of gastroduodenal disorders, diseases and adverse conditions caused thereby.

BACKGROUND ART

Gastric and duodenal ulcers affect a significant portion of the human population worldwide. Currently, the usual treatment for both gastric and duodenal ulcers involves treatment of the patient with histamine $H_2$ receptor antagonists ($H_2$ blockers). While the $H_2$ blocker therapy is generally effective in healing ulcers, ulcer relapse occurs in up to 90% of patients within a year of discontinuing the therapy. Thus, patients must continue the treatment for many years or risk a recurrence of the ulcer. It is now known that ulcer healing drugs such as colloidal bismuth subcitrate (CBS) are helicobactericidal and that such CBS is used in combination with $H_2$ blockers to treat ulcers. Additionally, CBS, an $H_2$ blocker and amoxicillin have been used in combination to treat ulcer patients.

*Helicobacter pylori* has been recently demonstrated to be a major causative agent in gastric and duodenal ulcers and other gastroduodenal disorders, diseases and adverse conditions. Thus, antibiotic therapy to eliminate *Helicobacter pylori* from the gastroduodenal tract would remove the root cause of said gastroduodenal disorders, diseases and adverse conditions and eliminate the need for an ulcer patient to continue long and costly treatment with $H_2$ blockers and the like. None of the foregoing treatments are capable of 100% eradication of *Helicobacier plyori*. Therefore, it would be desired to provide a compound having an excellent helicobactericidal activity.

The object of the present invention is to provide novel quinolone compounds having an excellent helicobactericidad activity and a pharmaceutical composition comprising the same. Another object of the present invention is to provide processes for producing the novel quinolone compounds.

BRIEF DESCRIPTION OF THE INVENTION

Accordingly, the present invention provides quinolone compounds of the formula:

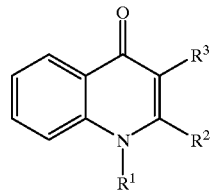
(I)

wherein R is a group of the formula:

$R^1$ is H, $R^2$ is

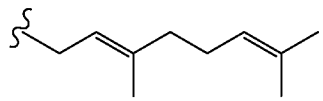

and $R^3$ is $CH_3$;

$R^1$ is $CH_3$, $R^2$ is

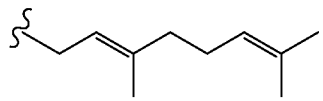

and $R^3$ is $CH_3$;

$R^1$ is $CH_2SCH_3$, $R^2$ is

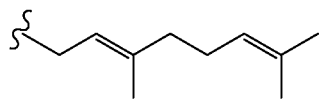

and $R^3$ is $CH_3$;

$R^1$ is $CH_3$, $R^2$ is

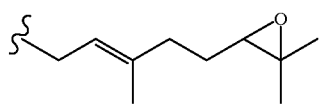

and $R^3$ is $CH_3$;

$R^1$ is H, $R^2$ is

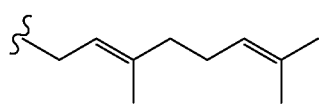

and $R^3$ is H;

$R^1$ is $CH_3$, $R^2$ is

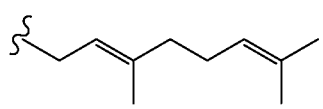

and $R^3$ is H;

$R^1$ is $CH_3$, $R^2$ is

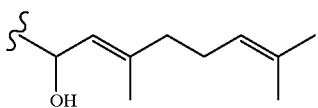

and $R^3$ is H; or
$R^1$ is $CH_3$, $R^2$ is

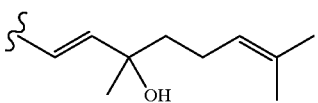

and $R^3$ is H.

Among the compounds of formula (I) of the present invention, preferred is a compound of formula (I) wherein $R^1$ is H, $R^2$ is

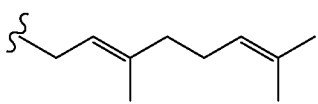

and $R^3$ is $CH_3$;
$R^1$ is $CH_3$, $R^2$ is

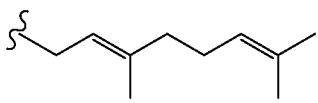

and $R^3$ is $CH_3$; or
$R^1$ is $CH_3$, $R^2$ is

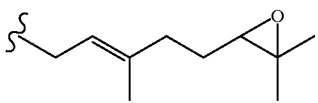

and $R^3$ is $CH_3$.

Among these compounds, most preferred is a compound of formula (I) wherein $R^1$ is H, $R^2$ is

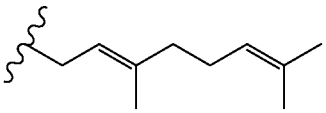

and $R^3$ is $CH_3$.

Further, the present invention provides processes for producing the quinolone compounds of formula (I), which comprise cultivating a microorganism having identifying characteristics of FERM BP-4785, or a mutant or recombinant form thereof. This process may further comprise the subsequent step of isolating said quinolone compounds from the fermentation broth.

The present invention is also directed to a culture which belongs to genus Amycolata being capable of producing quinolones, including the culture Amycolata sp. FERM BP-4785.

Also, the present invention provides a pharmaceutical composition for use in the treatment of *Helicobacter pylori*-induced disorders, diseases or adverse conditions caused thereby, which comprises compounds of formula (I) and a pharmaceutically-acceptable carrier.

Therefore, the present invention is useful for treatment of *Helicobacter pylori*-induced disorders, diseases or adverse conditions caused thereby, such as gastroduodenal disorders including gastric ulcer, duodenal ulcer and gastric cancer.

DETAILED DESCRIPTION OF THE INVENTION

The microorganism designated Amycolata sp. FERM BP-4785, which is useful for the preparation of compounds CJ-13,136, CJ-13,217, CJ-13,536, CJ-13,564, CJ-13,565, CJ-13,566, CJ-13,567 and CJ-13,568 (described below) was isolated from a soil sample collected in India. It is distinguished by the white aerial mycelium, the pale yellow to pale orange substrate mycelium, and the fragmentation of both aerial and substrate mycelium into spores. The results of whole-cell analyses further establish that it has a type IV of cell wall composition.

A culture thereof, designated herein as FERM BP-4785, was inoculated from a 14 day-old slant into Weinstein's broth and grown for 4 days at 28° C. on a shaker set at 200 rpm. It was then homogenized for 30 seconds, centrifuged for 20 min, washed 3 times with sterile distilled water, and planted on media commonly used for identification of members of the Actinomycetales. The culture was incubated at 28° C., and results were read at varying times but most commonly recorded at 14 days. The colors were determined by comparisons with color chips from Color Standards and Color Nomenclature, R. Ridgway, 1912. The methods of whole-cell amino acid and sugar analyses were those described in J. L. Staneck, and G. D. Roberts, (Appl. Microbiol., 28: 226–231, 1974). About 50 grams of autoclaved, wet mycelia of culture FERM BP-4785 were used for mycolate analysis, using the methods described in M. P. Lechevalier, A. C. Horan and H. Lchevalier, J. Bacteriol. 105: 313–318, 1971. The sample prepared was redissolved in hexane: t-butyl methyl ether (1:1) and injected into HP 5890 (Series II) gas chromatography; Menaquinones were isolated from 8.8 grams of wet cells killed by addition of formalin to a final concentration of 0.5% and standing at room temperature for one hour, then the cells extracted with chloroform-methanol (2:1) and chloroform-methanol (1:2) overnight with shaking. The crude extracts were combined, taken to dryness in vacuo at 50° C., spotted on silica gel TLC with a 254 nm fluorescent indicator and developed in a hexane:ethyl ether (85:15) system. UV-absorbing bands comigrating with a standard sample of vitamin $K_1$, were scraped off and eluted with chloroform. The components of these mixtures were determined by the molecular ions present in their mass spectra (HP 5989 Particle Beam Mass Spectrometer).

Media used for description of the cultures and references to their formulation were as follows:

1. Yeast Extract-Malt Extract Agar (ISP#2—Difco).
2. Oatmeal Agar (ISP#3—Difco).
3. Inorganic Salts-Starch Agar (ISP#4—Difco).
4. Glycerol-Asparagine Agar (ISP#5—Difco).
5. Czapek Sucrose Agar—ibid, medium 1, p. 328.
6. Glucose Asparagine Agar—S. A. Waksman, 1961, The Actinomycetes, Vol. 2, medium 2, p. 328.
7. Nutrient Agar—ibid, medium 14, p. 330.

8. Emerson's Agar—ibid, medium 28, p. 331.
9. Bennett's Agar—ibid, medium 30, p. 331.
10. Starch Agar—ibid.
11. Gelatin Agar—ibid.
12. Calcium Malate Agar—S. A. Waksman, Bacteriol. Rev. 21: 1–29, 1957.
13. Gordon and Smith's Tyrosine Agar—R. E. Gordon and M. M. Smith, J. Bacteriol. 69: 147–150, 1955.
14. Casein Agar—ibid.
15. Potato Carrot Agar—M. P. Lechevalier, J. Lab. and Clinical Med. 71: 934–944, 1968, but use only 30 g potatoes, 2.5 g carrots and 20 g agar.
16. 2% Tap Water Agar
17. Dextrose-Nitrate Broth—S. A. Waksman, 1961, The Actinomycetes, Vol. 2, medium 2, p. 328, with 3 g dextrose substituted for 30 g sucrose and agar omitted.
18. Organic Nitrate Broth—R. E. Gordon and J. M. Mihm. J. Bacteriol. 73: 15–27, 1957.
19. Skim Milk—Difco.
20. Hydrolysis of Hippurate and Esculin—R. E. Gordon et al., Int. J. Syst. Bacteriol. 24: 54–63, 1974.
21. Cellulose utilization—
    a) H. L. Jensen, Proc. Linnean Soc. N. S. Wales 55: 231–248, 1930.
    b) M. Levine and H. W. Schoenlein, A Compilation of Culture Media, medium 2511, 1930.
22. Decomposition of Adenine, Hypoxanthine, Xanthine, elastin and Urea—ibid.
23. Utilization of Organic Acids—ibid.
24. Carbohydrate Utilization and Acid Production from Carbohydrates—ibid.
25. Carbohydrates—ISP #9 medium, Difco.
26. Yeast Dextrose Agar for studies of Temperature, Resistance to Lysozyme and Survival at 50° C.—ibid.
27. Weinstein's Broth—glucose, 1 g; potato starch, 24 g; yeast extract, 5 g; tryptone, 5 g; beef extract, 3 g; calcium carbonate, 2 g; tap water, 1 L (pH=7.0).

Culture FERM BP-4785 exhibited the following characteristics:

Yeast Extract-Malt Extract Agar—Growth good to moderate, white; moderately raised, smooth to granular, aerial mycelium white; reverse maize yellow (IV) to light orange-yellow (III); no soluble pigment.

Oatmeal Agar—Growth poor to moderate, white; thin, smooth to slightly granular, aerial mycelium white; reverse colorless; no soluble pigment.

Inorganic Salts-Starch Agar—Growth poor to moderate, white; thin, smooth, aerial mycelium white; reverse colorless; no soluble pigment Glycerol-Asparagine Agar—Growth good, white, capucine buff, pale orange-yellow (III) to orange-pink (II); moderately raised to raised, smooth to granular, aerial mycelium white to orange-pink (II); reverse orange-buff (III) to light orange-yellow (III); no soluble pigment.

Czapek Sucrose Acar—Growth moderate, white; thin to slightly raised, smooth, aerial mycelium white; reverse colorless; no soluble pigment.

Glucose-Asparagine Agar—Growth moderate, white; thin to slightly raised, smooth to slightly granular, aerial mycelium white; reverse colorless; no soluble pigment.

Nutrient Agar—Growth moderate to good, white; thin to moderately raised, smooth to granular, aerial mycelium white; reverse colorless to maize yellow (IV); no soluble pigment.

Emerson's Agar—Growth moderate to good, white; moderately raised, smooth to granular, aerial mycelium white; reverse maize yellow (IV) to apricot yellow (IV); no soluble pigment.

Bennett's Agar—Growth good, white; moderately raised, smooth to granular, aerial mycelium white; reverse capucine buff (III); no soluble pigment.

Starch Aar—Growth moderate, white; thin to slightly raised, smooth, aerial mycelium white; reverse colorless to maize yellow (IV); no soluble pigment.

Gelatin Agar—Growth moderate to good, white; thin to moderately raised, smooth to granular, aerial mycelium white; reverse colorless to maize yellow (IV); no soluble pigment.

Calcium Malate Agar—Growth poor to moderate, white; thin, smooth, aerial mycelium white; reverse colorless; no soluble pigment.

Gordon and Smith's Tyrosine Agar—Growth moderate, white; thin to slightly raised, smooth, aerial mycelium white, reverse maize yellow (IV); soluble pigment warm buff (XV).

Casein Agar—Growth moderate, white; thin to slightly raised, smooth, aerial mycelium white; reverse white; no soluble pigment.

Potato Carrot Agar—Growth poor to moderate, white; thin to slightly raised, smooth, aerial mycelium white; reverse colorless; no soluble pigment.

2% Tap Water Agar—Growth poor, white; thin, smooth, aerial mycelium white; reverse colorless; no soluble pigment.

Morphological Properties—Morphological properties were observed on Bennett's agar 14 days after inoculation. Vegetative hyphae branched, 0.6–1.2 $\mu$m diam., may fragmenting into rods or elliptical units; aerial mycelium white, sporophores monopodially branched, occasionally verticillately branched, often aggregated into patches; spore chains straight, wavy, or flexuous, 5 to 30 spores per spore chain, spores oval, elliptical to rod-shaped, 1.2–1.8×0.8–1.1 $\mu$m.

Biochemical Properties—
  I. Gram-positive; non-acid fast, melanin production negative; production of hydrogen sulfide positive; nitrate reduction positive in organic nitrate broth but negative in dextrose nitrate broth; gelatin liquefaction negative; hydrolysis of starch and hippurate negative; hydrolysis of esculin, casein and urea positive; decomposition of cellulose negative; resistance to lysozyme positive; no clearing and no coagulation on milk; NaCl tolerance up to 3%; decomposition of adenine, elastin, hypoxanthine, xanthine and tyrosine negative.
  II. Utilization of organic acids—acetate, malate, propionate, pyruvate and succinate utilized, benzoate, citrate, lactate, mucate, oxalate, dextrin, and phenol not utilized.
  III. Acid production from carbohydrates—Acid produced from glucose and glycerol; acid not produced from adonitol, arabinose, cellobiose, dulcitol, erythritol, fructose, galactose, inositol, lactose, maltose, mannitol, melezitose, melibiose, α-methyl-d-glucoside, raffinose, ribose, rhamnose, salicin, sorbitol, starch, sucrose, trehalose and xylose.
  IV. Carbohydrate utilization—Glucose, and sucrose utilized; fructose, inositol, raffinose and rhamnose doubtfully utilized; arabinose, mannitol and xylose not utilized.

Temperature Relations—The culture grows at 21°, 28°, 37° and 45° C. It survives at 50° C. for 8 hours.

Cell Wall Analysis—The whole-cell hydrolysates contain meso-diaminopimelic acid, glucose, arabinose and galactose.

Mycolate Analyses—There were no mycolates present in the cell wall.

Menaquinone Analysis—The predominant menaquinone present in the cells was MK-8 (H4).

The culture FERM BP-4785 is characterized by the white aerial mycelium, the pale yellow to pale orange substrate mycelium, the fragmentation of the aerial and substrate mycelia into spores. Positive physiological reactions of the strain were: production of hydrogen sulfide; nitrate reduction in organic nitrate; hydrolysis of casein, esculin, and urea; resistance to lysozyme; formation of acid from glucose and glycerol; utilization of acetate, malate, propionate, pyruvate, succinate, glucose, sucrose; and survival at 50° C. for 8 hours. The strain did not decompose adenine, elastin, hypoxanthine, xanthine, tyrosine, cellulose, starch, and hippurate; it did not clear nor coagulate milk; melanin was not produced; nitrate was not reduced from dextrose nitrate broth; gelatin was not liquefied; starch and hippurate were not hydrolyzed; acid was not produced from adonitol, arabinose, cellobiose, dulcitol, erythritol, fructose, galactose, inositol, lactose, maltose, mannitol, melezitose, melibiose, α-methyl-D-glucoside, raffinose, ribose, rhamnose, salicin, sorbitol, starch, sucrose, trehalose and xylose; arabinose, mannitol and xylose were not used as sources of carbon.

The whole-cell analyses of the strain FERM BP-4785 revealed the presence of meso-diaminopimelic acid, arabinose, and galactose. Thus, it has the type IV cell wall composition and the type A whole-cell sugar pattern. These factors, together with the absence of mycolates in the cell wall and the presence of menaquinone MK-8 (H4) as the dominant component, indicate that the strain FERM BP-4785 belongs to the genus Amycolata, as defined by M. P. Lechevalier et al. (Int. J. Syst. Bacteriol. 36: 29–37, 1986).

Of the four species of Amycolata, the strain FERM BP-4785 is somewhat related to *A. hydrocarbonoxydans*. They are similar in the colors of the aerial and substrate mycelia, the negative decomposition of adenine, hypoxanthine, tyrosine and xanthine; the negative utilization of benzoate, citrate and mucate; the production of esculinase; and the failure to grow at 5% NaCl. However, the culture FERM BP-4785 differs in failure to liquefy gelatin, positive decomposition of casein, negative hydrolysis of starch, production of urease, resistance to lysozyme and ability to survive at 50° C.

Based on 16S rRNA sequence analysis, S. Warwick et al. (Int. J. Syst. Bacteriol. 44: 293–299, 1994) recently found that the sequences of members of Amycolata and Pseudonocardia were always recovered as a mixed group in phylogenetic trees and proposed that they be combined and classified in an emended genus Pseudonocardia. In this regard, it is worth noting that the strain FERM BP-4785 is similar to *Pseudonocardia thermophila* in both being able to survive at 50° C. Nevertheless, until this broaden definition of Pseudonocardia proposed by S. Warwick is universally accepted, the strain FERM BP-4785 is considered as a new strain of the genus Amycolata and designed as Amycolata sp. It was deposited under the accession number FERM BP-4785 to National Institute of Bioscience and Human-Technology, Agency of Industrial Science and Technology (located at 1–3 Higashi 1-chome, Tsukuba, Ibaraki 305, Japan) under the Budapest Treaty on Aug. 25, 1994.

In this invention, a mutant or recombinant form of FERM BP-4785 having the ability to produce the quinolone compounds of formula (I) can be also used. The mutant or recombinant form may be obtained by spontaneous mutation, artificial mutation with ultraviolet radiation, or treatment with mutagen such as N-methyl-N'-nitro-N-nitrosoguanidine or ethyl methanesulfonate, or a cell technology method such as cell fusion, gene manipulation or the like, according to well-known methods.

According to the present invention, the quinolone compounds of formula (I) may be produced by aerobic fermentation of FERM BP-4785, or a mutant or recombinant form thereof, under conditions similar to those generally employed to produce bioactive compounds by fermentation.

FERM BP-4785, or a mutant or recombinant form thereof, is usually fermented under submerged aerobic conditions with agitation at a temperature of 15 to 40° C. for 3 to 25 days, which may be varied according to scale and fermentation conditions such as medium and temperature. FERM BP-4785 is preferably fermented to produce said quinolone compounds in aqueous nutrient media at a temperature of 20 to 35° C. for 3 to 25 days. The pH of the medium may be adjusted in the range from 4.0 to 9.0, preferably from 5.0 to 7.5.

Nutrient media useful for fermentation include a source of assimilable carbon such as sugars, starches and glycerol; a source of organic nitrogen such as casein, enzymatic digest of casein, soybean meal, cotton seed meal, peanut meal, wheat gluten, soy flour, meat extract and fish meal; and a source of growth substances such as mineral salts, sodium chloride and calcium carbonate; and trace elements such as iron, magnesium, copper, zinc, cobalt and manganese. If excessive foaming is encountered during fermentation, anti-foam agents such as polypropylene glycols or silicones may be added to the fermentation medium.

Aeration of the medium in fermenters for submerged growth is maintained at 10 to 200%, preferably at 50 to 150% volumes of sterile air per volume of the medium per minute. The rate of agitation depends on the type of agitator employed. A shake flask is usually run at 150 to 250 rpm whereas a fermenter is usually run at 300 to 2,000 rpm. Aseptic conditions must, of course, be maintained through the transfer of the organism and throughout its growth.

The quinolone compounds thus produced may be isolated by standard techniques such as extraction and various chromatographic techniques.

The quinolone compounds CJ-13,136, CJ-13,217, CJ-13,536, CJ-13,564, CJ-13,565, CJ-13,566, CJ-13,567 and CJ-13,568 were isolated in a substantially pure form from the fermentation mixture, and identified by various spectroscopic techniques such as UV spectrophotometry, NMR and mass spectrometries. According to the analyses, these compounds are believed to have the following chemical formulas.

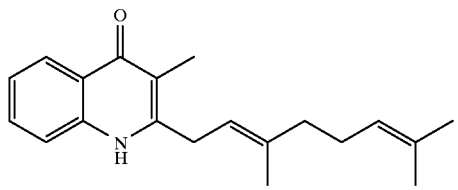

CJ-13,136

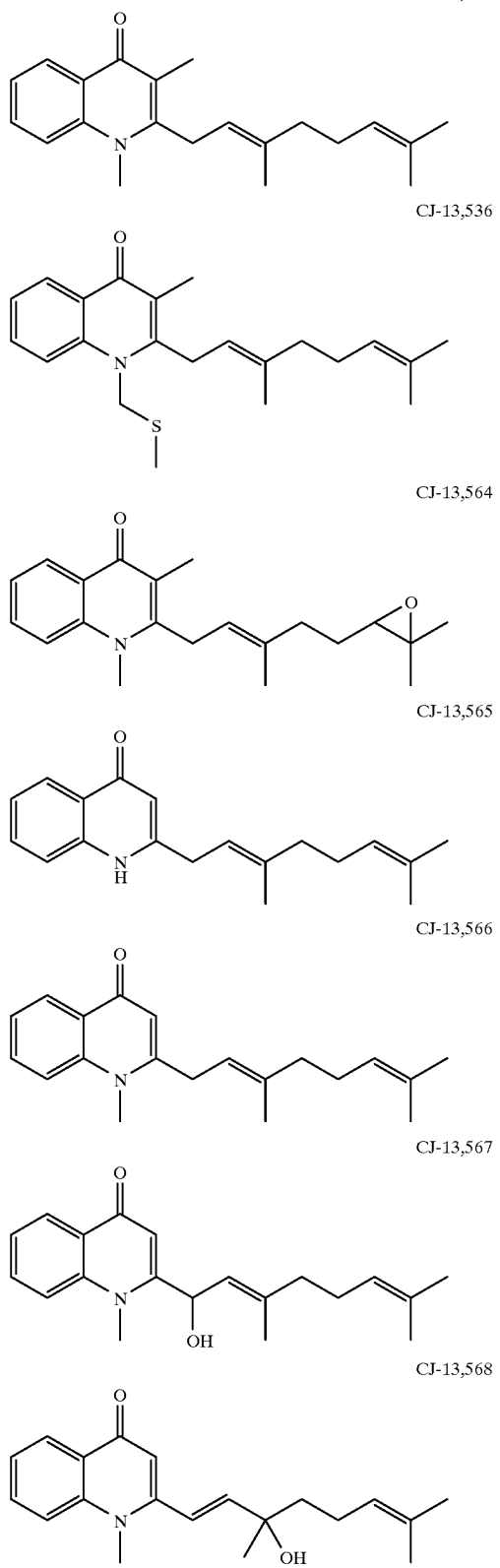

The helicobactericidal activity of the quinolone compounds of this invention was determined by an agar plate method using the paper disk (8 mm, ADVANTEC) and Brucella agar medium (BBL-Becton Dickinson Microbiology Systems). The quinolone compounds, CJ-13,136, CJ-13,217, CJ-13,536, CJ-13,564, CJ-13,565, CJ-13,566, CJ-13,567 and CJ-13,568 showed helicobactericidal activities. Among these compounds, CJ-13,136, CJ-13,217 and CJ-13,564 showed especially high activities. When tested against other microorganisms such as *Bacillus stearothermophilus, Micrococcus luieus, Staphylococcus aureus* and *Pasteurella haemolyrica* at the concentrations equivalent to those used in the above test, none of the quinolone compounds showed bactericidal activities against these microorganisms.

Accordingly, the quinolone compounds of formula (I) of the present invention are useful in the treatment of *Helicobacter pylori*-induced disorders, diseases or adverse conditions caused thereby, such as gastroduodenal disorders including gastric ulcer, duodenal ulcer and gastric cancer. For use as a helicobactericidal agent in a mammalian subject, especially a human subject, the quinolone compounds of formula (I) of the present invention can be administered either alone, or with an inert carrier in a pharmaceutical composition, according to standard pharmaceutical practice. The quinolone compounds of formula (I) of this invention may also be administered in combination with a suitable $H_2$ blocker such as ranitidine, cimetidine, famotidine or nizatinine, a proton pump inhibitor such as omeprazole, other antibiotic such as amoxicillin, or any combination thereof. If desired, CBS may be also added to the pharmaceutical composition. The compounds can be applied by parenteral or oral administration. The active ingredient may be compounded, for example, with the usual non-toxic, pharmaceutically-acceptable carriers for tablets, pellets, capsules, suppositories, solutions, emulsions, suspensions and other forms suitable for use.

The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations. In addition, if needed, auxiliary, stabilizing and coloring agents and perfumes may be used. In general, the quinolone compounds of this invention are present in such dosage forms at concentration levels ranging 5 to 70% by weight, preferably 10 to 50% by weight.

The quinolone compounds of formula (I) of this invention can be used in mammalian subjects as helicobactericidal agents in dosages ranging from 0.1 to 20 mg/kg. The dosage to be used in a particular case will vary according to a number of factors such as the disease state or condition being treated, the potency of the individual compound being administered, the response of the particular subject and the route of administration. The preferred route of administration is generally oral, but parenteral administration (e.g., intravenous, intramuscular, subcutaneous or intramedullary) will be preferred in special cases such as where oral administration is complicated by the patient's inability to ingest the drug. The effective daily amount ranges mentioned are therefore guidelines only and are not intended to limit the scope or use of the invention to any extent. However, when a quinolone compound of formula (I) is used in a human patient to treat gastroduodenal disorders, the usual dosage will be in the range from 0.5 to 250 mg and preferably 5 to 250 mg, one to four times per day.

EXAMPLES

The present invention is illustrated by the following examples. However, it should be understood that the invention is not limited to the specific details of these examples.

Spectral and physico-chemical data were obtained by the following instruments: UV, JASCO Ubest-30; IR, Shimadzu IR-470; NMR, JEOL JNM-GX270 updated with a LSI-11/73 host computer, TH-5 tunable probe and version 1.6 software; and LREI- and HREI-MS, Hitachi M-80 with an M-003 data processing system. All NMR spectra were measured in $CDCl_3$ unless otherwise indicated and peak positions are expressed in parts per million (ppm) based on the internal standard of the $CHCl_3$ peak at 7.24 ppm for $^1H$ NMR and 77.0 ppm for $^{13}C$ NMR. The peak shapes are denoted as follows: s (singlet), d (doublet), dd (doublet of doublet), ddd (doublet of doublet of doublet), t (triplet), q (quartet), m (multiplet), br (broad), brs (broad singlet), brd (broad doublet), brt (broad triplet) and sh (shoulder).

Example 1

Cells from a 10- to 21-day-old petri dish of Amycolata sp. FERM BP-4785 grown on ATCC #172 agar medium (glucose 1%, dextrin 2%, yeast extract 0.5%, NZ Amine type A 0.5%, $CaCO_3$ 0.1% and agar 1.5%) were harvested and suspended in 2 ml sterile water. This suspension was used to inoculate 100 ml of Medium-1 (glucose 2%, Polypepton 0.5%, beef extract 0.3%, wheat gluten 0.5%, yeast extract 0.5%, blood meal 0.3% and $CaCO_3$ 0.4%, pH 7.0–7.2) in a 500 ml flask. The flask was shaken at 26° C. for 4 days on a rotary shaker with 7-cm throw at 220 rpm, to obtain a first seed culture.

Three shake flasks containing Medium-1 (150 ml) were inoculated with 7.5 ml of the first seed culture. The flasks were shaken at 26° C. for 3 days on the rotary shaker, to obtain second seed cultures.

These second seed cultures were used to inoculate three 6-1 fermentation vessels containing 3 1 of Medium-2 (glucose 2%, dextrin 3%, Polypepton 0.5%, Polypepton-S 1%, corn steep powder 0.5%, NaCl 0.3%, $CaCO_3$ 0.3% and $CoCl_2$ 0.0001%, pH 6.4–6.6). Aeration was carried out at 26° C. for 9 days with agitation at 1,700 rpm and aeration at 3 1 per min Example 2

The procedure similar to that of Example 1 was repeated except that Medium-2 was replaced by Medium-3 (glucose 1%, corn starch 2%, wheat embryo 0.5%, NZ Amine type A 0.5%, yeast extract 0.5%, $CaCO_3$ 0.4% and $CoCl_2$ 0.0001%, pH 6.6–6.8).

Example 3

Isolation of Quinolone Compounds

The combined broth of the three 6-1 fermentation vessels of Example 2 was freeze-dried, and the resulting powder dissolved in 4.4 l of acetone-water (7:3). The solution was filtered, the filtrate was concentrated to aqueous solution (2 l), and extracted with 3.5 l of ethyl acetate. The extract was dried over anhydrous $Na_2SO_4$ and evaporated to afford an oily residue. The oily residue was loaded on a silica gel column and compounds were eluted with ethyl acetate-n-hexane (1:1) (1.5 l), then ethyl acetate-n-hexane (3:1) (1.5 l) and finally methanol (1.5 l). Fractions showing activity were applied separately to another silica gel column and eluted with the appropiate solvent. Fractions showing activity were then applied separately to a Sephadex LH-20 (Pharmacia trademark) column and eluted with methanol. Fractions showing activity were further applied to a YMC-pack ODS AM SH-343-5AM (Yamamura trademark) column (20×250 mm) and eluted with methanol-water (1:1 to 9:1) for 120 min at a flow rate of 10 ml/min. The detection was made by UV absorbance at 240 nm.

The eluted peaks showing activity were collected to yield the compounds CJ-13,136 (26.6 mg), CJ-13,217 (9.1 mg), CJ-13,536 (1.8 mg), CJ-13,564 (1.5 mg), CJ-13,565 (0.6 mg), CJ-13,566 (1.0 mg), CJ-13,567 (11.5 mg) and CJ-13,568 (1.8 mg). The eight compounds were separated by HPLC using a YMC-pack ODS AM-302 (Yamamura trademark) column (150×4.6 mm) and eluted with methanol-water (4:1) for 30 min at a flow rate of 1 ml/min at 40° C. The retention times (min) of the separated compounds were 5.4 (CJ-13,136), 6.0 (CJ-13,217), 8.5 (CJ-13,536), 2.7 (CJ-13,564), 4.3 (CJ-13,565), 4.6 (CJ-13,566), 3.5 (CJ-13,567) and 3.0 (CJ-13,568).

Characterization

The physico-chemical properties of CJ-13,136, CJ-13,217, CJ-13,536, CJ-13,564, CJ-13,565, CJ-13,566, CJ-13,567 and CJ-13,568 are as follows.

CJ-13,136 was isolated as colorless glass, and exhibited the following spectral data: HREI-MS (m/z) obs. 295.1924 (calcd. for $C_{20}H_{25}NO$, 295.1934); UV $\lambda_{max}$ (MeOH, nm) 335.2 ($\epsilon$ 9,400), 322.4 ($\epsilon$ 9,200), 242.4 ($\epsilon$ 26,300) and 213.4 ($\epsilon$ 25,400); IR (KBr, $cm^{-1}$) 3425, 2925, 1634, 1604, 1588, 1551, 1496, 1473, 1443, 1389, 1356, 1253, 997, 753, 689, 603, 565 and 430; LREI-MS (m/z) 295 (44.3%, rel. int.), 227 (73.5), 226 (100.0), 212 (52.1), 198 (12.0), 184 (21.7), 173 (54.8), 144 (6.9), 130 (5.1), 77 (6.7), 69 (16.4) and 41 (32.4); $^1H$ NMR (see Table 1); $^{13}C$ NMR (see Table 2).

CJ-13,217 was isolated as colorless glass, and exhibited the following spectral data: HREI-MS (m/z) obs. 309.2086 (cacld. for $C_{21}H_{27}NO$, 309.2090); UV $\lambda_{max}$ (MeOH, nm) 344.2 ($\epsilon$ 7,000), 331.4 ($\epsilon$ 6,400), 247.2 ($\epsilon$ 15,700) and 213.8 ($\epsilon$ 16,000); IR (KBr, $cm^{-1}$) 2920, 1616, 1593, 1568, 1541, 1495, 1465, 1366, 1298, 1192, 1108, 1032, 982, 935, 758, 691 and 427; LREI-MS (m/z) 309 (33.1%, rel. int.), 240 (100.0), 226 (29.1), 213 (15.5), 212 (25.3), 198 (37.4), 187 (21.9), 173 (7.4), 77 (7.1), 69 (13.0) and 41 (18.0); $^1H$ NMR (see Table 1); $^{13}C$ NMR (see Table 2).

CJ-13,536 was isolated as colorless glass, and exhibited the following spectral data: HREI-MS (m/z) obs. 355.1952 (cacld. for $C_{22}H_{29}NOS$, 355.1968); UV $\lambda_{max}$ (MeOH, nm) 343.8 ($\epsilon$ 23,900), 331.2 ($\epsilon$ 20,600), 247.4 ($\epsilon$ 42,800) and 211.6 ($\epsilon$ 38,100); IR (KBr, $cm^{-1}$) 2925, 1618, 1598, 1551, 1488, 1474, 1455, 1447, 1436, 1417, 1373, 1265, 1194, 1156, 1095, 1078, 1049, 1034, 986 and 758; LREI-MS (m/z) 355 (48.8%, rel. int.), 308 (50.5), 294 (12.6), 286 (7.3), 272 (10.6), 240 (96.8), 226 (19.0), 224 (24.7), 212 (15.9), 198 (33.3), 184 (9.1), 173 (11.3), 132 (11.0), 77 (21.5), 69 (81.7), 61 (100.0) and 41 (59.6); $^1H$ NMR (see Table 1); $^{13}C$ NMR (see Table 2).

CJ-13,564 was isolated as colorless glass, $[\alpha]_D^{25}$ −17.5° (c 0.04, MeOH), and exhibited the following spectral data: HREI-MS (m/z) obs. 325.2060 (cacld. for $C_{21}H_{27}NO_2$, 325.2041); UV $\lambda_{max}$ (MeOH, nm) 344.0 ($\epsilon$ 15,800), 332.0 ($\epsilon$ 15,700), 246.0 ($\epsilon$ 39,700) and 214.4 ($\epsilon$ 38,200); IR (KBr, $cm^{-1}$) 2930, 1616, 1597, 1539, 1505, 1471, 1386, 1304, 1197, 1110, 1078 and 760; LREI-MS (m/z) 325 (14.6%, rel. int.), 310 (2.1), 240 (100.0), 226 (14.0), 212 (5.5), 210 (5.2), 198 (17.2), 77 (4.7), 59 (5.0) and 41 (4.6); $^1H$ NMR (see Table 1); $^{13}C$ NMR (see Table 2).

CJ-13,565 was isolated as colorless glass, and exhibited the following spectral data: HREI-MS (m/z) obs. 281.1788 (cacld. for $C_{19}H_{23}NO$, 281.1781); UV $\lambda_{max}$ (MeOH, nm) 328.0 ($\epsilon$ 12,700), 316.0 ($\epsilon$ 13,100), 238.4 ($\epsilon$ 34,700) and 212.6 ($\epsilon$ 37,100); IR (KBr, $cm^{-1}$) 2920, 1643, 1597, 1547, 1504, 1473, 1444, 1378, 1353, 1321, 1246, 1158, 1136, 1106, 766 and 589; LREI-MS (m/z) 281 (34.1%, rel. int.), 213 (100.0), 212 (56.5), 198 (50.0), 196 (16.9), 172 (28.9), 159 (60.2), 130 (6.7), 89 (6.5), 77 (8.5), 69 (21.5) and 41 (31.5); $^1H$ NMR (see Table 1).

CJ-13,566 was isolated as colorless glass, and exhibited the following spectral data: HREI-MS (m/z) obs. 295.1940 (cacld. for $C_{20}H_{25}NO$, 295.1935); UV $\lambda_{max}$ (MeOH, nm) 335.4 ($\epsilon$ 14,700), 322.8 ($\epsilon$ 14,200), 241.6 ($\epsilon$ 31,500) and 213.6 ($\epsilon$33,400); IR (KBr, $cm_{-1}$) 2925, 1630, 1600, 1574, 1554, 1498, 1470, 1442, 1413, 1276, 1174, 1150, 1106, 1073, 836 and 758; LREI-MS (m/z) 295 (75.0%, rel. int.), 226 (100.0), 212 (92.1), 198 (61.8), 186 (38.7), 184 (63.6), 173 (92.9), 159 (63.6), 144 (13.0), 130 (12.3), 115 (10.1), 89 (14.1), 77 (23.8), 69 (30.5), 53 (11.2) and 41 (73.7); $^1$H NMR (see Table 1).

CJ-13,567 was isolated as colorless glass, $[\alpha]_D^{25}$ +66.3° (c 0.575, MeOH), and exhibited the following spectral data: HREI-MS (m/z) obs. 311.1887 (cacld. for $C_{20}H_{25}NO_2$, 311.1883); UV $\lambda_{max}$ (MeOH, nm) 336.8 ($\epsilon$ 17,500), 324.4 ($\epsilon$ 16,400), 242.8 ($\epsilon$ 37,000) and 213.6 ($\epsilon$ 38,000); IR (KBr, $cm^{-1}$) 3230, 2920, 1622, 1600, 1565, 1500, 1469, 1440, 1414, 1383, 1346, 1306, 1267, 1202, 1175, 1154, 1087, 1038, 904, 847, 759, 672 and 469; LREI-MS (m/z) 311 (47.7%, rel. int.), 294 (8.6), 243 (51.7), 242 (38.3), 228 (48.1), 226 (100.0), 214 (6.5), 212 (14.1), 210 (9.4), 202 (18.6), 200(42.7), 198 (28.3), 189 (25.2), 184 (24.1), 174 (15.1), 173 (18.7), 160 (26.4), 159 (46.4), 158 (12.9), 144 (10.9), 130 (15.3), 89 (16.5), 77 (18.1), 69 (29.9) and 41 (64.6); $^1$H NMR (see Table 1); 13C NMR (see Table 2).

CJ-13,568 was isolated as colorless glass, $[\alpha]_D^{25}$ −51.4° (c 0.035, MeOH), and exhibited the following spectral data: HREI-MS (m/z) obs. 311.1886 (cacld. for $C_{20}H_{25}NO_2$, 311.1883); UV $\lambda_{max}$ (MeOH, nm) 338.8 ($\epsilon$ 15,200), 330 (sh), 252.4 ($\epsilon$38,600) and 218.6 ($\epsilon$ 23,500); IR (KBr, $cm^{-1}$) 3365, 2925, 1619, 1597, 1558, 1497, 1470, 1443, 1411, 1315, 1271, 1177, 1155, 1113, 1073, 1036, 978 and 758; LREI-MS (m/z) 311 (43.1%, rel. int.), 296 (17.0), 294 (13.3), 252 (15.6), 240 (23.6), 238 (54.5), 228 (27.4), 226 (12.2), 212 (11.3), 210 (13.2), 200 (15.6), 198 (20.1), 186 (100.0), 184 (36.5), 173 (38.5), 159 (11.2), 144 (6.2), 130 (5.3), 115 (6.3), 77 (14.1), 69 (8.7), 55 (14.9) and 43 (15.6); $^1$H NMR (see Table 1).

TABLE 1

$^1$H NMR spectral data of the quinolones.

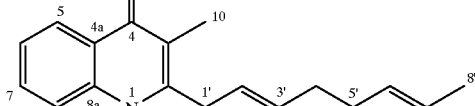

| Atom | CJ-13,136 | | | CJ-13,217 | | |
|---|---|---|---|---|---|---|
| No. | δ (ppm) | M | J (Hz) | δ (ppm) | M | J (Hz) |
| 1 | 8.17 | brs | | | | |
| 5 | 8.35 | dd | 8.3, 1.3 | 8.47 | dd | 8.1, 1.6 |
| 6 | 7.27 | dd | 8.3, 7.3 | 7.32 | dd | 8.1, 6.8 |
| 7 | 7.50 | ddd | 8.1, 7.0, 1.3 | 7.60 | ddd | 8.4, 6.8, 1.6 |
| 8 | 7.17 | d | 8.1 | 7.45 | d | 8.4 |
| 9 | | | | 3.71 | s | |
| 10 | 2.14 | s | | 2.21 | s | |
| 1' | 3.47 | d | 7.7 | 3.55 | d | 6.2 |
| 2' | 5.33 | t | 7.3 | 5.04 | m | |
| 4' | 2.18 | m | | 2.06 | m | |
| 5' | 2.18 | m | | 2.06 | m | |
| 6' | 5.11 | m | | 5.04 | m | |
| 8' | 1.70* | s | | 1.77* | s | |

TABLE 1-continued $^1$H NMR spectral data of the quinolones.

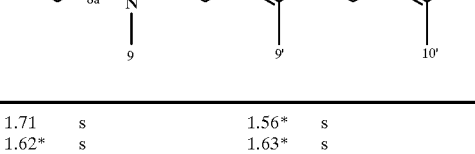

| | | | | | | |
|---|---|---|---|---|---|---|
| 9' | 1.71 | s | | 1.56* | s | |
| 10' | 1.62* | s | | 1.63* | s | |

| Atom | CJ-13,536 | | | CJ-13,564 | | |
|---|---|---|---|---|---|---|
| No. | δ (ppm) | M | J (Hz) | δ (ppm) | M | J (Hz) |
| 5 | 8.44 | brd | 7.8 | 8.47 | dd | 8.2, 1.7 |
| 6 | 7.59* | m | | 7.32 | dd | 8.2, 6.9 |
| 7 | 7.32* | m | | 7.61 | ddd | 8.8, 6.9, 1.8 |
| 8 | 7.59* | m | | 7.46 | d | 8.4 |
| 9 | 5.11 | s | | 3.72 | s | |
| 9-SMe | 2.19 | s | | | | |
| 10 | 2.19 | s | | 2.21 | s | |
| 1' | 3.67 | d | 5.7 | 3.58 | d | 6.2 |
| 2' | 5.06 | m | | 5.12 | m | |
| 4' | 2.07 | m | | 2.20 | m | |
| 5' | 2.07 | m | | 1.65 | m | |
| 6' | 5.06 | m | | 2.66 | m | |
| 8' | 1.80** | s | | 1.26* | s | |
| 9' | 1.57** | s | | 1.81 | s | |
| 10' | 1.64** | s | | 1.24* | s | |

| Atom | CJ-13,565 | | | CJ-13,566 | | |
|---|---|---|---|---|---|---|
| No. | δ (ppm) | M | J (Hz) | δ (ppm) | M | J (Hz) |
| 1 | 8.21 | brs | | | | |
| 3 | 6.17 | brs | | 6.26 | s | |
| 5 | 8.32 | brd | 8.1 | 8.43 | dd | 8.1, 1.4 |
| 6 | 7.30 | m | | 1.35 | dd | 7.8, 7.0 |
| 7 | 7.55 | brt | 7.7 | 7.64 | ddd | 8.9, 7.0, 1.4 |
| 8 | 7.30 | m | | 7.48 | d | 8.9 |
| 9 | | | | 3.69 | s | |
| 1' | 3.40 | d | 6.8 | 3.41 | d | 6.8 |
| 2' | 5.32 | t | 7.7 | 5.20 | t | 6.8 |
| 4' | 2.13 | m | | 2.07 | m | |
| 5' | 2.13 | m | | 2.07 | m | |
| 6' | 5.08 | m | | 5.04 | m | |
| 8' | 1.72* | s | | 1.71* | s | |
| 9' | 1.57* | s | | 1.58* | s | |
| 10' | 1.61* | s | | 1.63* | s | |

| Atom | CJ-13,567 | | | CJ-13,568 | | |
|---|---|---|---|---|---|---|
| No. | δ (ppm) | M | J (Hz) | δ (ppm) | M | J (Hz) |
| 3 | 6.35 | s | | 6.37 | s | |
| 5 | 8.22 | dd | 7.8, 1.5 | 8.43 | dd | 8.1, 1.4 |
| 6 | 7.28 | dd | 8.0, 7.2 | 7.36 | dd | 8.1, 7.0 |
| 7 | 7.44 | ddd | 8.6, 7.2, 1.6 | 7.66 | ddd | 8.6, 7.0, 1.9 |
| 8 | 7.11 | d | 8.6 | 7.48 | d | 8.4 |
| 9 | 3.64 | s | | 3.74 | s | |
| 1' | 5.44* | d | 7.8 | 6.74 | d | 15.1 |
| 1'-OH | 5.17 | brs | | | | |
| 2' | 5.38* | d | 7.6 | 6.35 | d | 15.4 |
| 4' | 2.05 | m | | 1.7 | m | |
| 5' | 2.05 | m | | 2.1 | m | |
| 6' | 5.01 | m | | 5.13 | m | |
| 8' | 1.68** | s | | 1.68* | s | |
| 9' | 1.53** | s | | 1.38 | s | |
| 10' | 1.61** | s | | 1.60* | s | |

M: multiplicity.
*,**: interchangable with assignments marked by the same characters.

TABLE 2

$^{13}$C NMR spectral data of the quinolones.

[Structure of quinolone with numbered atoms: quinoline core with positions 1-8a, 4-oxo (position 4), methyl at 10 (position 3), N-methyl at 9, and geranyl-type chain at position 2 with carbons 1'-10']

| Atom No. | CJ-13,136 δ (ppm) | CJ-13,217 δ (ppm) | CJ-13,536 δ (ppm) | CJ-13,564 δ (ppm) | CJ-13,567 δ (ppm) |
|---|---|---|---|---|---|
| 2 | 145.9 | 150.6 | 149.8 | 150.3 | 155.6 |
| 3 | 115.6 | 117.4 | 118.2 | 117.4 | 111.0 |
| 4 | 177.9 | 177.2 | 177.4 | 177.2 | 178.4 |
| 4a | 123.8 | 124.9 | 124.9 | 124.9 | 125.5 |
| 5 | 123.4* | 122.8* | 123.6* | 122.8* | 123.6* |
| 6 | 126.4* | 127.0* | 127.2* | 127.0* | 125.9* |
| 7 | 131.1 | 131.5 | 131.6 | 131.5 | 132.0 |
| 8 | 116.6 | 115.0** | 115.6** | 115.0** | 115.2 |
| 8a | 143.6 | 141.1 | 140.3 | 141.1 | 141.7 |
| 9 |  | 34.8 | 49.6 | 11.7 | 35.0 |
| 9-SMe |  |  | 14.4 |  |  |
| 10 | 10.2 | 11.6 | 11.5 | 34.9 |  |
| 1' | 30.6 | 30.6 | 30.1 | 30.6 | 70.0 |
| 2' | 116.6 | 118.3** | 118.6** | 118.7** | 123.0* |
| 3' | 138.3 | 139.0 | 139.5 | 138.4 | 141.7 |
| 4' | 39.6 | 39.4 | 39.4 | 36.3 | 39.6 |
| 5' | 26.4 | 26.4 | 26.3 | 27.4 | 6.1 |
| 6' | 123.1* | 123.7* | 123.2* | 63.9 | 123.2* |
| 7' | 132.5 | 131.9 | 131.9 | 58.2 | 132.0 |
| 8' | 25.8 | 25.7 | 25.7 | 24.8 | 25.7 |
| 9' | 16.5 | 16.5 | 16.5 | 16.6 | 17.0 |
| 10' | 17.8 | 17.7 | 17.7 | 18.7 | 17.7 |

*,**: interchangable with assignments marked by the same characters.

We claim:

1. A quinolone compound of the formula:

[Structure (I): quinolin-4(1H)-one with $R^3$ at position 3, $R^2$ at position 2, $R^1$ on N]

wherein $R^1$ is H, $R^2$ is

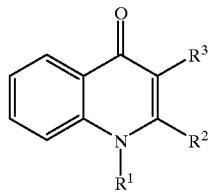

and $R^3$ is $CH_3$;

$R^1$ is $CH_3$, $R^2$ is

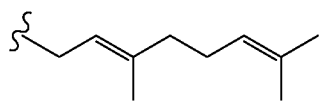

and $R^3$ is $CH_3$;

$R^1$ is $CH_2SCH_3$, $R^2$ is

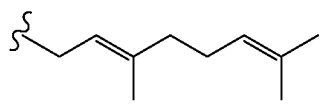

and $R^3$ is $CH_3$;

$R^1$ is $CH_3$, $R^2$ is

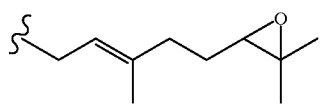

and $R^3$ is $CH_3$;

$R^1$ is H, $R^2$ is

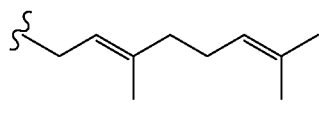

and $R^3$ is H;

$R^1$ is $CH_3$, $R^2$ is

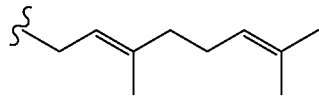

and $R^3$ is H;

$R^1$ is $CH_3$, $R^2$ is

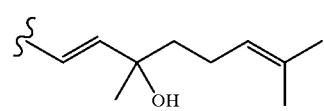

and $R^3$ is H; or $R^1$ is $CH_3$, $R^2$ is

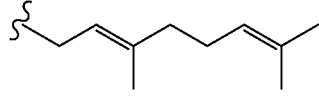

and $R^3$ is H.

2. A quinolone compound according to claim 1, wherein $R^1$ is H, $R^2$ is

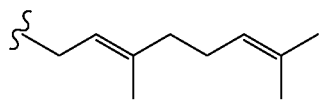

and $R^3$ is $CH_3$;

$R^1$ is $CH_3$, $R^2$ is

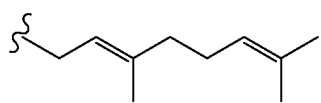

and $R^3$ is $CH_3$; or $R^1$ is $CH_3$, $R^2$ is

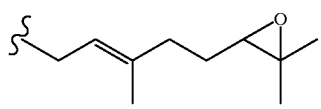

and $R^3$ is $CH_3$.

3. A quinolone compound according to claim 2, wherein $R^1$ is H, $R^2$ is:

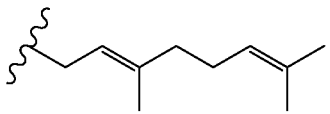

and $R^3$ is $CH_3$.

4. A process for producing quinolone compounds according to claim 1, which comprises cultivating a microorganism having the identifying characteristics of Amycolata sp. FERM BP-4785, or a mutant or recombinant form thereof.

5. A process according to claim 4, which further comprises the subsequent step of isolating said quinolone compounds from the fermentation broth.

6. A pharmaceutical composition for use in the treatment of *Helicobacter pylori*-induced disorders, diseases or adverse conditions caused thereby, which comprises a compound according to claim 1 and a pharmaceutically-acceptable carrier.

* * * * *